United States Patent
Inoue et al.

(10) Patent No.: US 7,090,755 B2
(45) Date of Patent: Aug. 15, 2006

(54) GAS DETECTING DEVICE WITH SELF-DIAGNOSIS FOR ELECTROCHEMICAL GAS SENSOR

(75) Inventors: Tomohiro Inoue, Minoo (JP); Yuki Fujimori, Minoo (JP)

(73) Assignee: Figaro Engineering Inc., Osaka (JP)

( * ) Notice: Subject to any disclaimer, the term of this patent is extended or adjusted under 35 U.S.C. 154(b) by 69 days.

(21) Appl. No.: 11/041,291

(22) Filed: Jan. 25, 2005

(65) Prior Publication Data

US 2006/0091007 A1 May 4, 2006

(30) Foreign Application Priority Data

Oct. 28, 2004 (JP) .............................. 2004-313829

(51) Int. Cl.
*G01N 27/404* (2006.01)
(52) U.S. Cl. .................. 204/401; 204/432; 73/1.06
(58) Field of Classification Search ................ 204/401, 204/431, 432; 73/1.06
See application file for complete search history.

(56) References Cited

U.S. PATENT DOCUMENTS

| | | | |
|---|---|---|---|
| 5,202,637 A | 4/1993 | Jones | |
| 5,611,909 A * | 3/1997 | Studer | ......................... 205/775 |
| 5,733,436 A * | 3/1998 | Demisch et al. | ............ 205/775 |
| 6,123,818 A | 9/2000 | Lindsay | |
| 6,200,443 B1 | 3/2001 | Shen et al. | |
| 6,251,243 B1 | 6/2001 | Lindsay | |
| 6,428,684 B1 * | 8/2002 | Warburton | ................... 205/775 |
| 6,896,781 B1 | 5/2005 | Shen | |
| 7,033,482 B1 * | 4/2006 | Inoue | ......................... 205/775 |
| 2003/0145644 A1 | 8/2003 | Rabbett et al. | |
| 2005/0121338 A1 | 6/2005 | Inoue | |

FOREIGN PATENT DOCUMENTS

| | | |
|---|---|---|
| JP | 61-212753 | 9/1986 |
| JP | 04-190154 | 7/1992 |
| JP | 2004-061171 | 2/2004 |

* cited by examiner

*Primary Examiner*—Kaj K. Olsen
(74) *Attorney, Agent, or Firm*—Rothwell, Figg, Ernst & Manbeck, P.C.

(57) ABSTRACT

A test signal is applied in parallel with an electrochemical gas sensor for about ten seconds, while an amplifying circuit is turned off. After turning off the test signal, the amplifying circuit is turned on. If the gas sensor outputs an waveform of a predetermined shape in a predetermined period after the turning-on, the gas sensor will be judged to be normal.

6 Claims, 8 Drawing Sheets

GAS DETECTING DEVICE WITH SELF-DIAGNOSIS FOR ELECTROCHEMICAL GAS SENSOR

FIELD OF THE INVENTION

The present invention relates to self-diagnosis of an electrochemical gas sensor.

BACKGROUND ART

Document 1 through document 3 disclose self-diagnosis using capacitance of an electrochemical gas sensor. Document 1 and document 2 relate to a gas sensor using liquid electrolyte, and a pulse test signal is inputted into an amplifier rather than the gas sensor. The gas sensor is connected to another input of the amplifier in parallel with a fixed resistor, the amplifier changes its output according to the input of the test signal, and the transfer function of this process changes according to the capacity of the gas sensor. As the capacity of the gas sensor changes depending on whether the sensor is normal or not, the gas sensor can be diagnosed on the basis of the output of the amplifier.

In document 3, a pulse voltage is applied to a gas sensor, and self-diagnosis is made on the basis of the output waveform of the sensor after the end of the pulse. To be more specific, as the normal gas sensor has a large capacity and the defective gas sensor has a smaller capacity, the gas sensor can be checked on the basis of the relaxing speed of the output after the end of the pulse.

| Document 1 | USP6251243 |
| Document 2 | USP6123818 |
| Document 3 | USP6200443 |

SUMMARY OF THE INVENTION

An object of the invention is to provide a new self-diagnosing device for an electrochemical gas sensor.

In the present invention, a gas detecting device having an electrochemical gas sensor having at least a sensing electrode and a counter electrode connected to a solid or liquid electrolyte, and an amplifying circuit for amplifying the output of the gas sensor to detect a gas, wherein said gas sensor is self-diagnosed upon the output of said gas sensor upon applying an electrical test signal thereto, the gas detecting device further comprises:

test signal applying means for applying the test signal to the gas sensor when the amplifying circuit is not operating;

sampling means for starting up said amplifying circuit when said test signal turns off and for sampling the output of said amplifying circuit within a predetermined period after said startup; and self-diagnosing means for self-diagnosing said gas sensor upon the output of the sampling means.

The electrolyte to be used in an electrochemical gas sensor may be a liquid electrolyte such as aqueous solution of sulfuric acid or potassium hydroxide or metallic salt, or an ionic liquid. As for the startup of the amplifying circuit, preferably, it is made concurrently with the end of the test signal or after that, and much more preferably, the amplifying circuit is started up after the end of the test signal.

Preferably, the self-diagnosing means diagnoses said gas sensor as normal when the output of the sampling means is within a predetermined range different from the output in clean air and diagnoses said gas sensor as abnormal when the output of the sampling means is within a second predetermined range in the vicinity of the output in clean air or in the vicinity of both ends of the output range of said amplifying circuit.

Preferably, the device further comprises a resistor connected in parallel with said gas sensor.

Preferably, either one electrode of the sensing electrode and the counter electrode of the gas sensor is kept at a constant potential by means of the power source of the gas detecting device, the other electrode of the gas sensor is connected to the input of an operational amplifier of said amplifying circuit, and said device further comprises an FET switch having a source, a drain, and a gate arranged in parallel with the gas sensor and opening when the voltage between the source and the drain is not less than a predetermined value, wherein the gate is arranged so that the voltage is not less than the predetermined value when the power source is on and is less than the predetermined value when the power source is off.

Preferably, the device further comprises a switch, opening while a test signal is being applied, between said the other electrode and the input of the operational amplifier.

More preferably, the test signal applying means applies the test signal from said the other electrode into the gas sensor.

In the present invention, the electrochemical gas sensor can be self-diagnosed easily, in particular, the state of the gas sensor can be diagnosed whether it is normal or abnormal due to, for example, short-circuit, breaking of wire, electrode deterioration or dry-up.

When a resistor is connected in parallel with the gas sensor, polarization of the sensor while left without any power source can be prevented, and it becomes easier to apply a very small test signal to the gas sensor.

Either one electrode of the sensing electrode and the counter electrode of the gas sensor is kept at a constant potential by means of the power source of the gas detecting device, the other electrode of the gas sensor is connected to the input of the operational amplifier of the amplifying circuit, the source and the drain of an FET switch, which opens when the voltage between the source potential and the gate potential is not lower than a predetermined value, are arranged in parallel with the gas sensor, and the gate is arranged so that the voltage between the source and the gate of the FET switch is not lower than a predetermined value when the power source is on and the voltage between the source and the gate of the FET switch is less than the predetermined value when the power source is off. As a result, when the power source is on, the FET switch will open and will not operate, and when the power source is off, the FET switch will close to connect both electrodes of the gas sensor and prevent polarization.

The operational amplifier has an offset, and when a resistor is arranged in parallel with the operational amplifier to prevent polarization of the gas sensor, both the inputs of the operational amplifier will be connected by the resistor. In an operational amplifier, which has an offset and operates at a high gain, when the voltages of both the inputs are completely equal to each other, a large offset voltage will be outputted. When the gas sensor is parallel-connected with the FET switch, and the power supply is on and the switch is opened, both inputs of the operational amplifier will be connected by the gas sensor of non-ohmic resistance, thus the output voltage due to the offset can be reduced. Accordingly, restrictions regarding the operational amplifier are reduced, and the circuit cost can be reduced significantly.

Here, preferably, a switch, which will open when the test signal is applied, is provided between the other electrode and the input of the operational amplifier, the connection between the gas sensor and the amplifying circuit can be opened/closed by the switch. When one electrode of the gas sensor is connected to a power source through a potentiostat circuit and the other electrode is connected to an operational amplifier, the potentiostat circuit seems a buffer or the like and is provided with the operational amplifier. When the operational amplifier as the buffer connected to a power source and the operational amplifier for amplifying sensor signals is connected to another power source, the two packages for two operational amplifiers are needed. However, when the switch for stopping an input of the sensor signals to the operational amplifier is provided, two operational amplifiers may be provided in one package with a common power source. Therefore, one package for one of the operational amplifiers may be omitted.

Much more preferably, if the test signal applying means applies a test signal from the other electrode to the gas sensor, the test signal applying means can easily apply a small test signal to the gas sensor, thus deterioration of the electrolyte or electrodes and hysteresis can be prevented.

| Brief Description of the Symbols | |
|---|---|
| 2 | Gas sensor |
| 4 | Electrolyte membrane |
| 6 | Counter electrode |
| 8 | Sensing electrode |
| 10, 12 | Porous conductive membranes |
| 14 | Counter electrode plate |
| 16 | Sensing electrode plate |
| 20 | Power source |
| 22 | Microcomputer |
| 24 | Self-diagnosing part |
| 26 | Gas detecting part |
| 28 | Input/output |
| 30 | Zener diode |

| -continued | |
|---|---|
| Brief Description of the Symbols | |
| 32, 33 | FET switches |
| Tr1, Tr2 | Transistors |
| R1–R12 | Resistors |
| C1–C7 | Capacitors |
| VR1, VR2 | Variable resistors |
| IC1–IC3 | Operational amplifiers |
| Vcc | Amplifying circuit power source |
| A | Earth |
| P1, P2 | Control signals |
| P3 | Output |

EMBODIMENT

Figure 1:
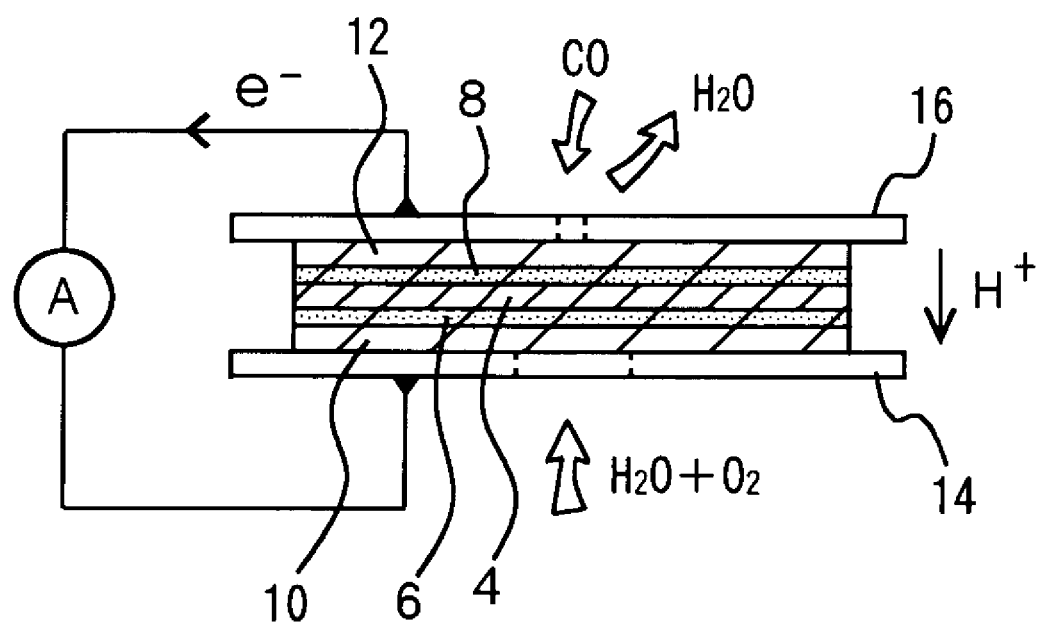
FIG. 1 is a sectional view of an important portion of an electrochemical gas sensor used in the embodiment.

FIG. 1 through FIG. 7 illustrate an embodiment. In FIG. 1, 2 denotes an electrochemical gas sensor, and 4 denotes an electrolyte membrane which may be a solid electrolyte membrane such as a polymer proton conductive membrane or a membrane of a liquid electrolyte held in a separator. The liquid electrolyte may be an aqueous electrolyte wherein an electrolyte such as sulfuric acid, KOH, $MgSO_4$ is dissolved in water, or may be an organic electrolyte, in particular, an ionic liquid may be used. When a liquid electrolyte is used, it is not necessarily essential to use the electrolyte in a membrane form; for example, it may be stored in an appropriate vessel.

6 denotes a counter electrode, and 8 denotes a sensing electrode. Here the counter electrode 6 and the sensing electrode 8 are provided on both the faces of the electrolyte membrane 4, respectively, but they may be arranged on one face thereof with a space between them. In the counter electrode 6 or the sensing electrode 8, a noble metal catalyst such as Pt or Pt—Ru is supported by minute carbon particulates and a binder is added to them, and if necessary, a solid or liquid electrolyte is added. 10 and 12 denote porous conductive membranes, and here they are hydrophobic carbon sheets or carbon papers. 14 denotes a counter electrode plate and 16 denotes a sensing electrode plate. The counter electrode plate 14 is provided with a hole illustrated by a broken line, and the counter electrode plate 14 is supplemented with water vapor or a liquid electrolyte and oxygen from a liquid reservoir not illustrated. The sensing electrode 16 is also provided with a hole illustrated by a broken line, and a gas to be detected such as CO is introduced through the hole, and $CO_2$ or the like, generated by the reaction at the sensing electrode, is discharged through the hole as well. The counter electrode plate 14 and the sensing electrode plate 16 are, for example, metal plates. A current generated by the electrode reaction at the sensing electrode 8 will be amplified to detect the gas.

Figure 2:
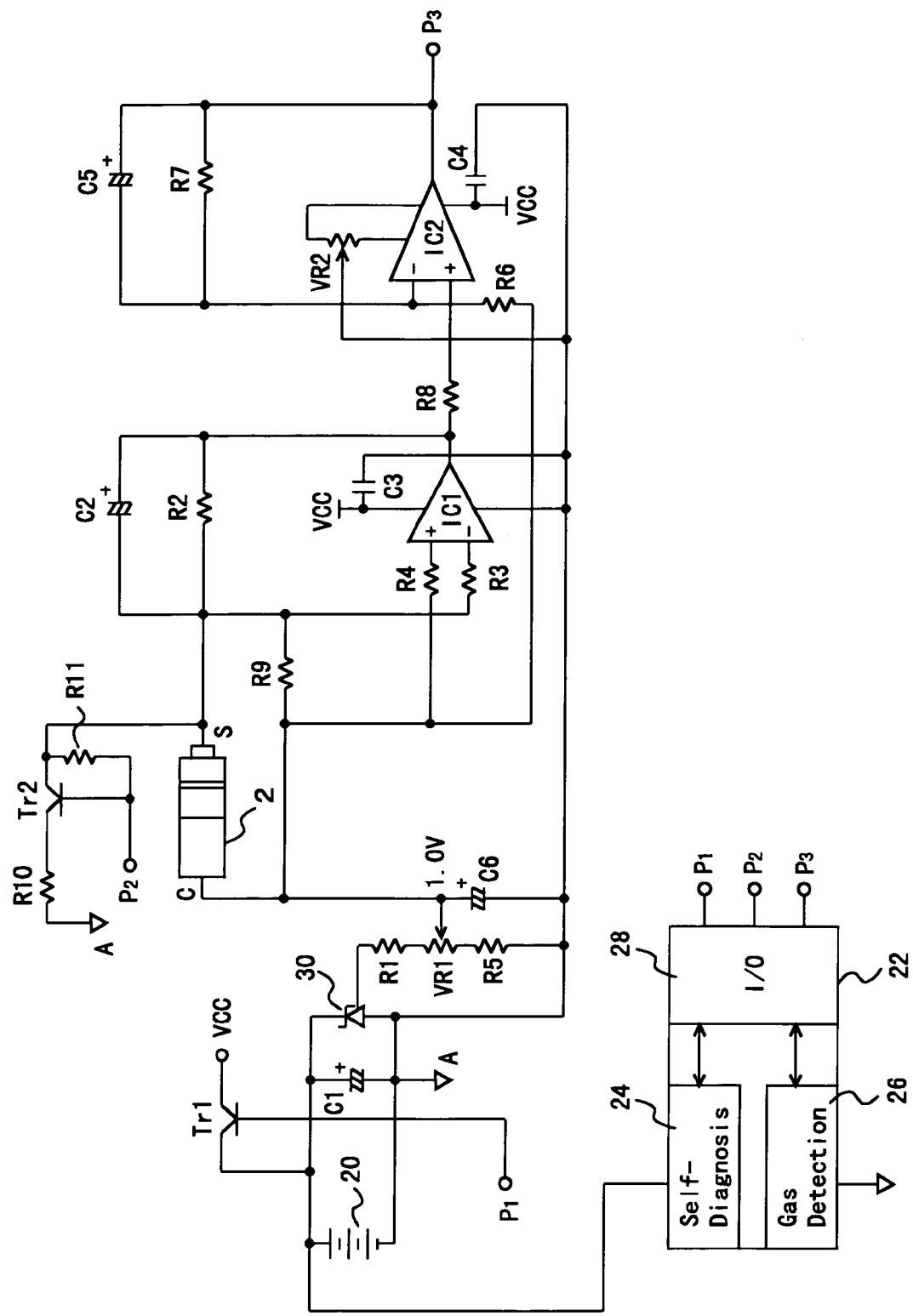
FIG. 2 is a circuit diagram of the gas detecting device with self-diagnosis of the embodiment.

FIG. 2 illustrates a circuit of the gas detecting device with self-diagnosis. 20 denotes a power source, and for example, here it is a battery power source of 5 V or 3 V or the like. 22 denotes a microcomputer provided with a self-diagnosing part 24, a gas detecting part 26 and an input/output 28. 30 denotes a Zener diode of which output is about 2 to 3 V. Tr1 and Tr2 are transistors and may be substituted with switches of a different kind,. R1 through R11 are resistors. Of these resistors, the resistor R9 is a resistor of, for example, about 100 Ω to 10 kΩ, and the resistor R10 is a resistor of a fairly high resistance in comparison with the resistor R9 so that the voltage being applied to the gas sensor 2 is a sufficiently small value when the transistor Tr2 is turned on to connect the resistor R10 to earth A. This voltage is here about 1 mV, and preferably, about 10 µV to 100 mV. C1 through C6 denote capacitors, and VR1 and VR2 are variable resistors. In FIG. 2, the counter electrode of the gas sensor 2 is marked with C and the sensing electrode thereof is marked with S. The variable resistor VR1 is adjusted so that the counter electrode C is kept at a constant potential of, for example, 1 V.

IC1 and IC2 are operational amplifiers. For example, the sensing electrode S of the gas sensor 2 is connected to the inverted input, and the output of the gas sensor 2 is amplified in two stages of the operational amplifiers IC1 and IC2. The gain in this case is set in such a way that when a current of 1 µA flows in the gas sensor 2, the output P3 will change by 3 V. Vcc denotes an amplifying circuit power source and is supplied from the power source 20 via the transistor Tr1. Vcc is the power source of the operational amplifiers IC1 and IC2 and is also the power source of the amplifying circuit of the gas sensor 2.

In the circuit of FIG. 2, the counter electrode of the gas sensor 2 is kept at, for example, a constant potential of 1.0 V, and the sensing electrode S is connected to the inverted input of the operational amplifier IC1 via the resistance R3. The resistance R9 is connected in parallel to the gas sensor 2, and a parallel part comprising the gas sensor 2 and the resistance R9, in particular, its sensing electrode S is earthed via the transistor Tr2 and the resistor R10 of about 1 MΩ. The control signal for the transistor Tr2 is P2, and turning on the Tr2 is referred to as applying a test signal. Here, the resistance ratio of the resistor R10 and the resistor R9 is 1000:1, and for example, about 10:1 to 100000:1. When the transistor Tr2 is turned on and a short initial relaxation time is passed, a very small voltage will be applied to the gas sensor 2. It is one of the roles of the resistor R9 to keep the voltage applied to the gas sensor 2 to a very small value, when the test signal is applied. Another role of the resistor R9 is to prevent polarization of the gas sensor 2 when the power source 20 is off.

The self-diagnosing part 24 of the microcomputer 22, at an appropriate period, turns on the transistor Tr2 for ten seconds by, for example, the control signal P2 and turns off the amplifying circuit power source Vcc by the control signal P1. Preferably, while the transistor Tr2 is turned on, the transistor Tr1 is turned off. The transistor Tr2 is turned on for ten seconds and then the transistor Tr2 is turned off, and, for example, concurrently with it, and preferably, after the transistor Tr2 is turned off, with an interval of about 1 millisecond to 100 seconds, and more preferably, with an interval of about 10 milliseconds to 10 seconds, the transistor Tr1 is turned on. The self-diagnosing part 24 self-diagnoses the gas sensor 2 on the basis of the waveform of the output P3 within a predetermined time, for example, for ten seconds after the transistor Tr1 is turned on. In this way, the self-diagnosing part 24 controls the amplifying circuit power source Vcc with the control signal P1, controls the test signal with the control signal P2 and takes the output P3 through the input/output 28 to make self-diagnosis.

In the embodiment, the counter electrode C kept at a constant potential of, for example, the 1 V. However, the sensing electrode S may be kept at the constant potential, and the counter electrode C may be connected to the inverting input of the transistor Tr2 and the operational amplifier IC1. In the embodiment, since the gas sensor 2 is amperometric one, its output is connected to the inverting input of the operational amplifier IC1. However, the output voltage of gas sensor 2 may be used, and its output may be connected to the non-inverting input. Furthermore, in the embodiment, the two operational amplifiers IC1 and IC2 are used, but other than this, for example, a constant potential of 1 V may be generated with an operational amplifier for buffer. The test signal is inputted via the transistor Tr2, however, it may be directly inputted, for example, through the input/output 28. Moreover, as to the test signal, the current is arranged to flow from the resistor R9 to the resistor R10, however, the polarity of the test signal may be reversed. Furthermore, the gas sensor 2 is not limited to gas sensors of the two-electrode type, namely, a sensing electrode and a counter electrode. A gas sensor of a three-electrode type, namely, with a reference electrode beside them, may be used.

The operations of the gas detecting device under normal conditions will be described. The transistor Tr1 is on and the transistor Tr2 is off. If a gas such as CO or hydrogen or alcohol diffuses to the sensing electrode S, a current will flow from the sensing electrode S to the counter electrode C. A current equal to this current will flow through the resistor R2, in this case 100 kΩ. Accordingly, for example, when a current of 1 µA flows in the gas sensor 2, the potential of the output of the operational amplifier IC1 will change by 100 mV, and the potential of the non-inverted input of the operational amplifier IC2 will increase by 100 mV. Hence, on the operational amplifier IC 2, the voltage across the resistor R6 will be, for example, 100 mV, and if the resistance of the resistor R7 is set at 30 times of that of the resistor R6, the output P3 of the operational amplifier IC2 will increase, for example, by +3 V.

With an appropriate frequency, for example, once a day or once a week, the self-diagnosing part 24 of the microcomputer 22 turns on the transistor Tr2, for example, for ten seconds, while turning on the transistor Tr1. The self-diagnosing part 24 turns on the transistor Tr1, concurrently turns off the transistor Tr2, and preferably, turns on the transistor Tr1 after passage of about 1 millisecond to 100 seconds after the turning off of the transistor Tr2. When the self-diagnosing part 24 will turn on the transistor Tr1 again, and will self-diagnose the gas sensor 2 on the basis of the output P3 in a predetermined period after the turning on of the transistor Tr1.

Figure 3:
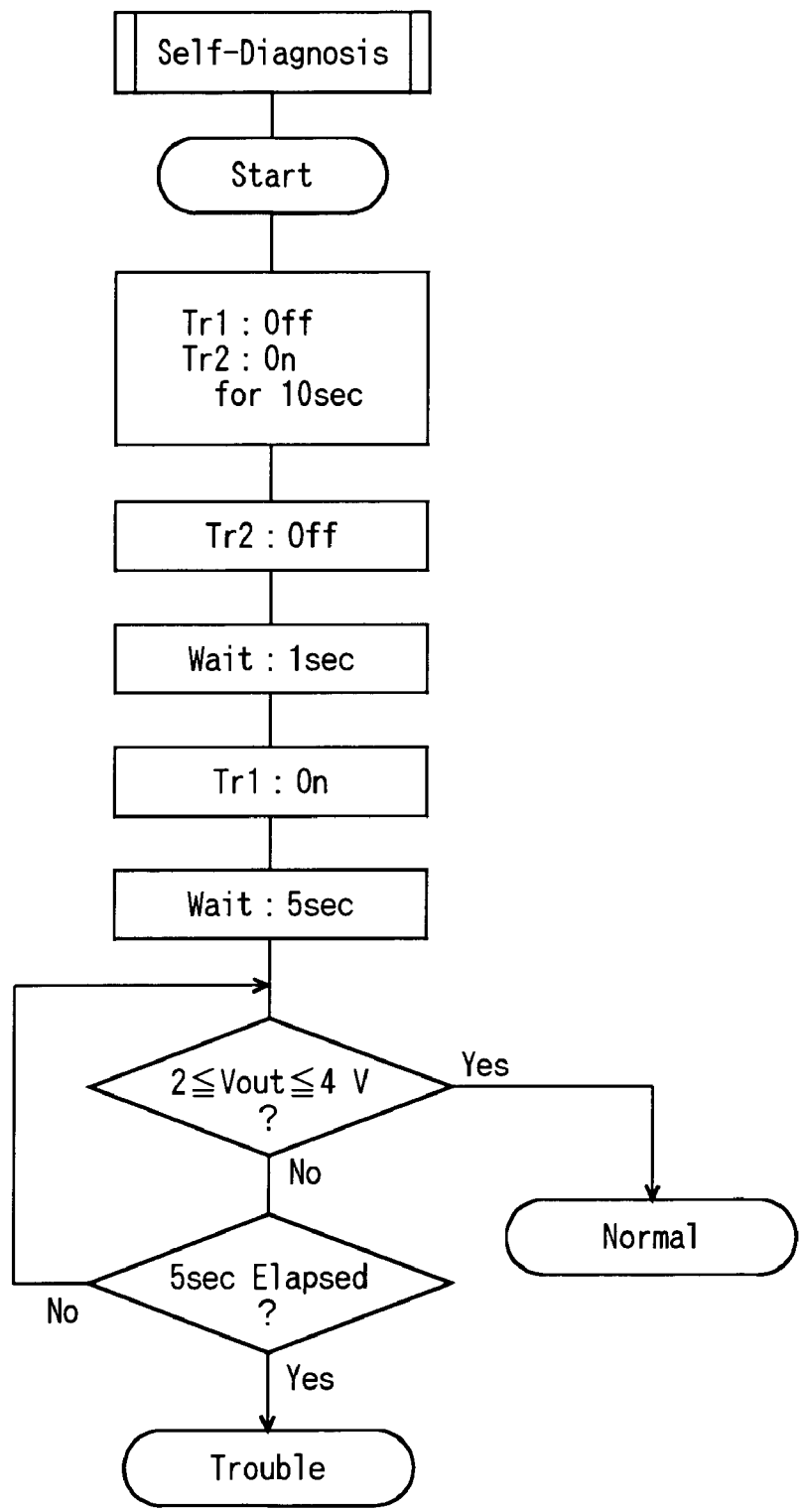
FIG. 3 is a flow chart illustrating the self-diagnosis algorithm in the embodiment.
Figure 4:
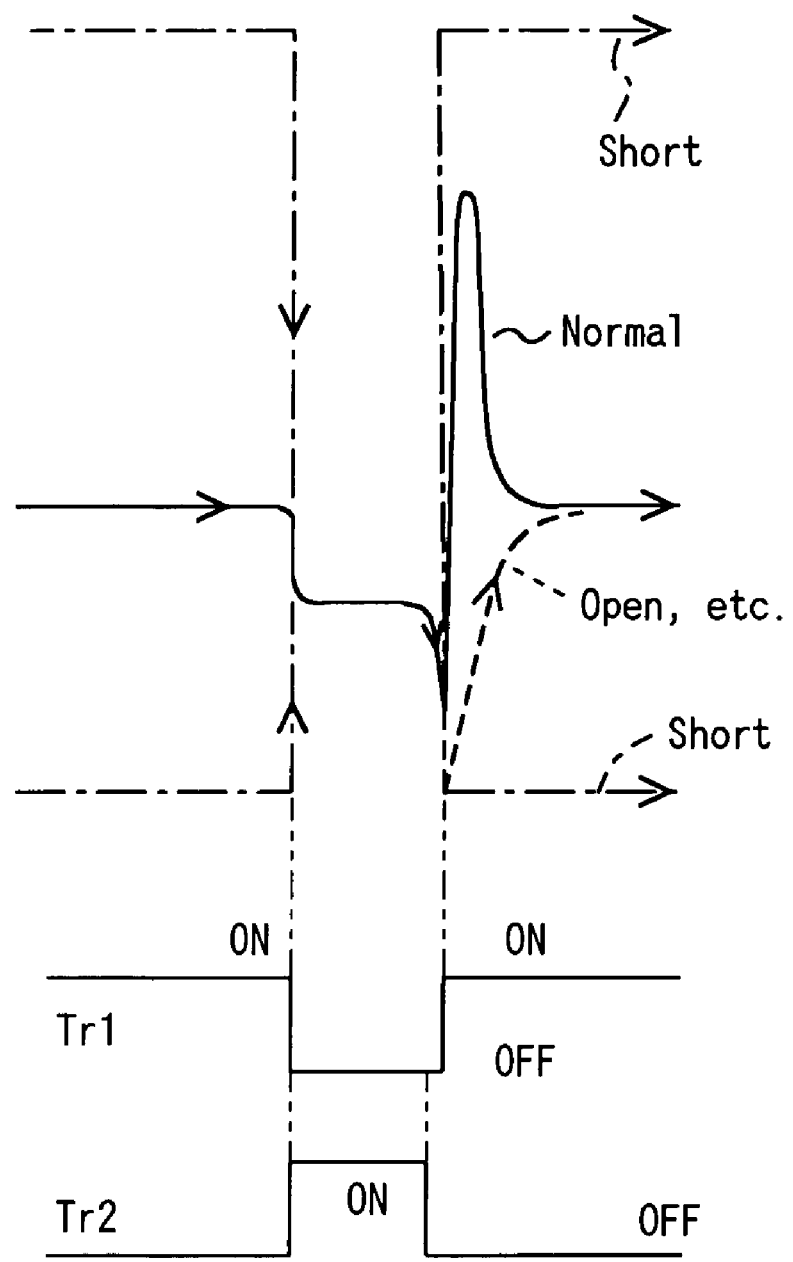
FIG. 4 is a timing chart illustrating the sensor outputs and actions of the respective transistors in the self-diagnosis of the embodiment.

FIG. 3 and FIG. 4 illustrate the self-diagnosis algorithm. The transistor Tr1 is turned off and the transistor Tr2 is turned on, for example, for 10 seconds. Next, the transistor Tr2 is turned off, and after waiting, for example, for one second, the transistor Tr1 is turned on. Immediately after turning on the transistor Tr1, there will be transient phenomena until the operational amplifiers IC1 and IC2 become stable, and until the voltages of the capacitors C2 through C5 become stable. Hence there is a step of waiting, for example, for five seconds. The waiting period may be zero, and preferably, the waiting period is not longer than ten seconds.

The output P3 (Vout) will be checked whether it is within a predetermined range of from 2 to 4 V in a period of five seconds after the transistor Tr1 is turned on, and if the output P3 is within the range even once, the gas sensor will be judged to be normal. If the output P3 is always less than 2 V or over 4 V during the period of five seconds, the gas sensor will be judged to have abnormality. Here, the output ranges of the operational amplifiers IC1, IC2 are within a range of from 0 to 5 V, and the value of the output P3 in clean air is 1 V. The gas sensor 2 may be judged defective when its abnormality is detected, for example, a plurality of times, and the gas sensor 2 may not be judged to be defective when its abnormality is detected only once.

As shown in FIG. 4, when the transistor Tr1 is turned off and the transistor Tr2 is turned on, the output P3 and the counter electrode C will be connected to each other via the resistors R6, R7, etc. Hence the output P3 will become substantially a constant value of less than 1 V. During this period except the time immediately after the transistor Tr2 is turned on, the voltage that is applied to the gas sensor 2 is determined by the ratio of the resistor R10 and the resistor R9. Hence a very small voltage, for example, about 1 mV will be applied to the gas sensor 2. Even such a small voltage can form electrical double layers between the electrolyte and the electrodes of the gas sensor. As the test signal to be applied to the gas sensor 2 is a very small one, it will not cause hysteresis or the like.

When the transistor Tr2 is turned off and then the transistor Tr1 is turned on, a current will flow, for example, from the sensing electrode S to the counter electrode C to neutralize the electric double layers formed in the gas sensor 2 by the test signal, and this in turn will generate a signal of which polarity is the same with that appears with a reducing gas, at the output P3. As this signal disappears when the electric double layers are eliminated, it appears as a temporary pulse signal, and the gas sensor 2 can be confirmed to be normal by detecting this signal.

For example, when the gas sensor 2 suffers from breaking, when the gas sensor 2 is not inserted, when the electrolyte membrane of the gas sensor 2 is abnormal due to drying-up or the like or when the electric electrodes of the gas sensor 2 are deteriorated, the output signals will be just as shown by broken lines in FIG. 4. This is due to lack of the current that cancels the electric double layers that should have been generated in the gas sensor 2 by the test signal. If the gas sensor 2 is short-circuited, when the transistor Tr1 is turned on, the output P3 will appear on either end of the output range. To self-diagnose the circuit such as the operational amplifier IC1 or IC2, it is sufficient to check for occurrence of a change in the output in concurrence with on/off of the transistors Tr1, Tr2.

Figure 5:
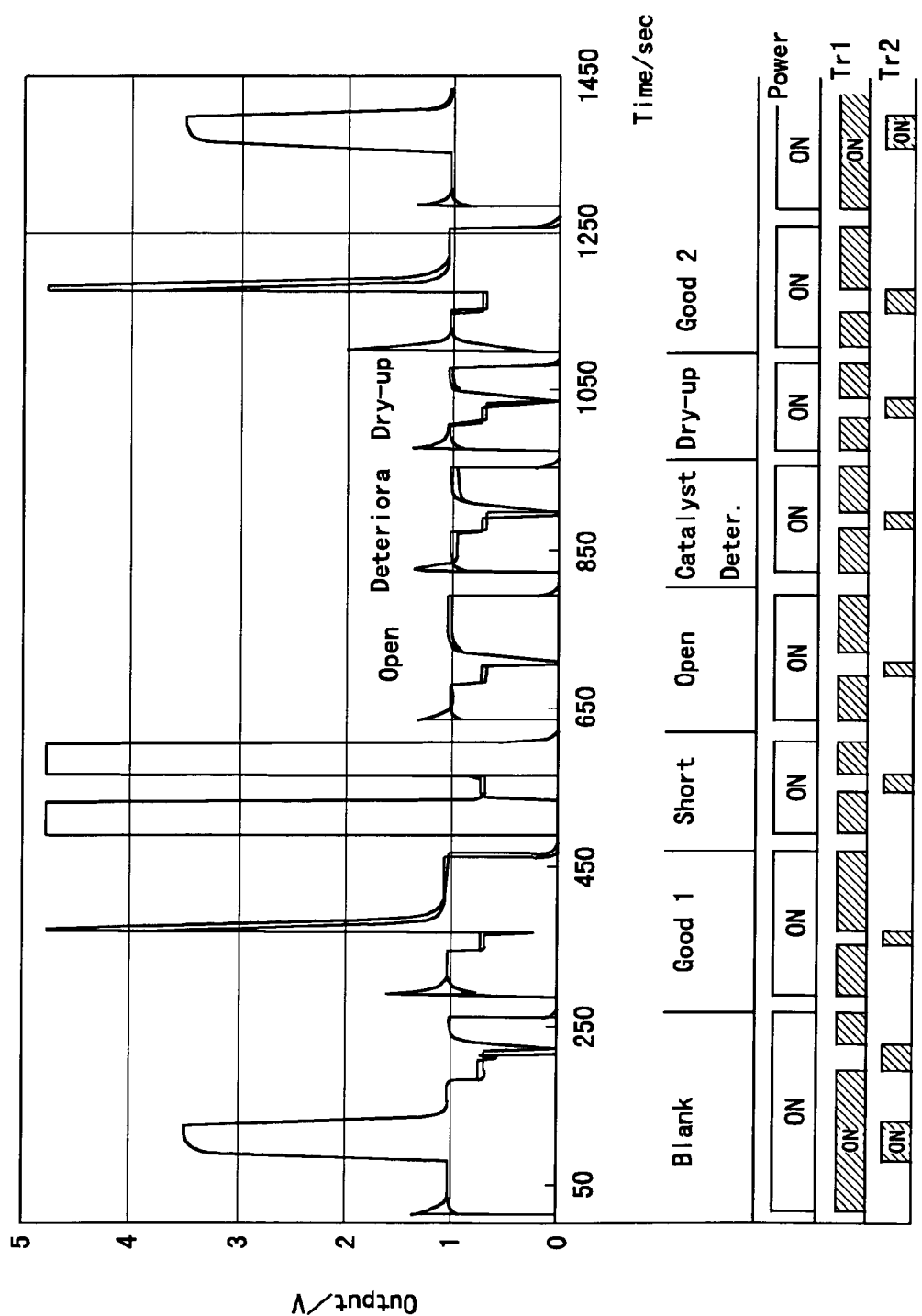
FIG. 5 is a characteristic diagram illustrating results of self-diagnosis of two gas sensors in the embodiment.

FIG. 5 illustrates the results of self-diagnosis of two gas sensors. Shown in the figure are the outputs P3 of FIG. 2, and 1 V is the output corresponding to measurement in clean air. "Blank" indicates the gas sensors having been removed. "Good 1" and "Good 2" indicate normal gas sensors having been installed, respectively. In "Good 1" and "Good 2", the two gas sensors were switched to each other.

"Short" indicates that gas sensors were short-circuited, and "Open" indicates that gas sensors having breaking of wire were mounted. "Catalyst Deteriorated" indicates an example wherein gas sensors with deteriorated catalyst were used. Here in place of deteriorated catalyst in gas sensors, electrodes of carbon supporting no noble metal were used for the sensing electrodes and the counter electrodes. "Dry-up" indicates that the electrolyte became abnormal because, for example, the gas sensors were not replenished with water vapor, or the liquid electrolyte was not replenished. Here, the liquid reservoirs were emptied to prevent the KOH aqueous solution contained in the separator from being replenished with water vapor, then the sensors were dried in dry air of 50°C. for two hours to serve as a "Dry-up."

The line of "Power" of FIG. 5 indicates ON/OFF of the battery power source. As for the ON/OFF of Tr1 and Tr2, the shaded state indicates ON, and the other state is OFF. In the gas sensor used, the electrolyte was KOH aqueous solution of 0.1 N, and it was held in a hydrophilic separator. When the electrolyte was a proton conductor or a solid electrolyte or sulfuric acid aqueous solution, similar results were obtained.

In the state of "Good 1" and "Good 2", the transistor Tr1 was kept off and the transistor Tr2 was kept on for ten seconds, then the transistor Tr2 was turned off, and one second after that, the transistor Tr1 was turned on. At that time, the output of the gas sensors exhibited a peak pulse of which peak width at half height was from about 5 to 20 seconds. In contrast to this, in the cases of gas sensors with breaking of wire, gas sensors with deteriorated catalyst, or dried-up gas sensors, when the transistor Tr2 was turned off and then the transistor Tr1 was turned on, the output P3 decreased once to about 0 V, then exponentially relaxed toward 1 V of output of the sensors in clean air. On the other hand, in the case of the short-circuited gas sensors, when the transistor Tr1 was on, the output read a value that was close either to 0V or 5 V Whether the value is close to 0 V or to 5 V is attributed to detailed constants of the circuits and dispersion in the operational amplifiers IC1, IC2, and the like.

In the case of the "Blank" wherein no gas sensors were inserted, the transistor Tr1 was turned off and the transistor Tr2 was turned on for ten seconds, then the transistor Tr2 was turned off, and then the transistor Tr1 was turned on. As a result, like the case of breaking of wire, the output reduced once to 0 V and then exponentially relaxed toward 1 V. On the other hand, in the state of "Blank," when both the transistors Tr1 and Tr2 were turned on, the output P3 increased to a little over 3 V. In the state of "Good 2," when both the transistor Tr1 and the transistor Tr2 were turned on, the output similarly increased to a little over 3 V. Accordingly, it was found that self-diagnosis of the gas sensor could not be done when the transistor Tr2 was turned on and the test signal was applied with the transistor Tr1 being kept on.

Next, before turning off the transistor Tr2, if the transistor Tr1 is turned on, as shown in the case of "Blank," the output P3 will tend to increase to a little over 3 V Hence this peak and the peak generated in a normal gas sensor will overlap with each other, making it difficult to diagnose them. Accordingly, it is desirable that the transistor Tr1 is turned on just when the transistor Tr2 is turned off or after the transistor Tr2 is turned off. Preferably, after the transistor Tr2 is turned off, after 1 msec to 100 sec, and much more preferably, after 10 msec to 10 sec, the transistor Tr1 is turned on.

In detecting pulses that are generated from a normal gas sensor, after the transistor Tr1 is turned on again, if there is a sensor signal at least once within a range of 2 to 4 V in a period of 5 to 10 seconds, it is judged that there is a pulse. In place of such a detecting method, it may be arranged to detect that the output P3 crosses a line of 2 V or the like from below upward and once more crosses the line from above downward within about ten seconds after the transistor Tr1 is turned on again. Thus the pulse detection method itself is discretionary. In the embodiment, after the transistor Tr1 is turned on again, if the output P3 does not reach a range of 2 to 4 V, it is judged to be abnormal, and during this period, if the output is held in a range of 0 to 2 V, the gas sensor is judged to be abnormal. Beside these cases, when the gas sensor output is fixed around 0 V, or when the output is fixed at 4 V or over, the gas sensor is judged to be abnormal. The window for detecting pulse is determined according to the kind of sensor and test conditions. As the time period from turning off the transistor Tr2 to turning on the transistor Tr1 is known, it may be arranged to detect pulse within a predetermined time window from turning off the transistor Tr2.

Figure 6:
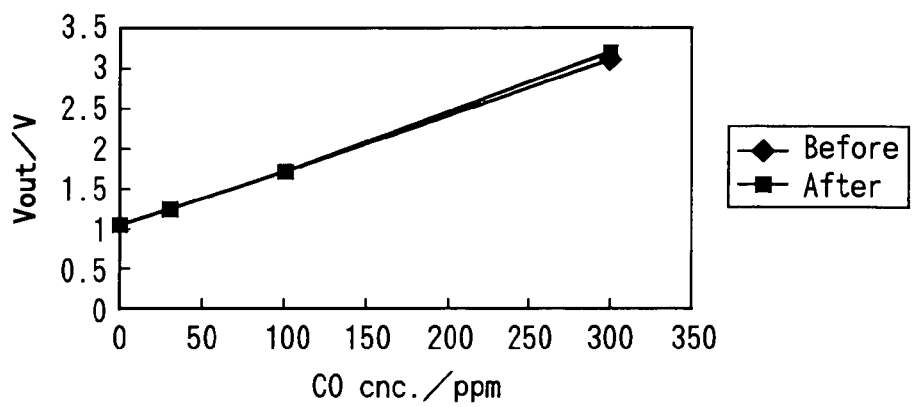
FIG. 6 is a characteristic diagram illustrating outputs of the gas sensor before and after conducting self-diagnosis ten times in the embodiment.
Figure 7:
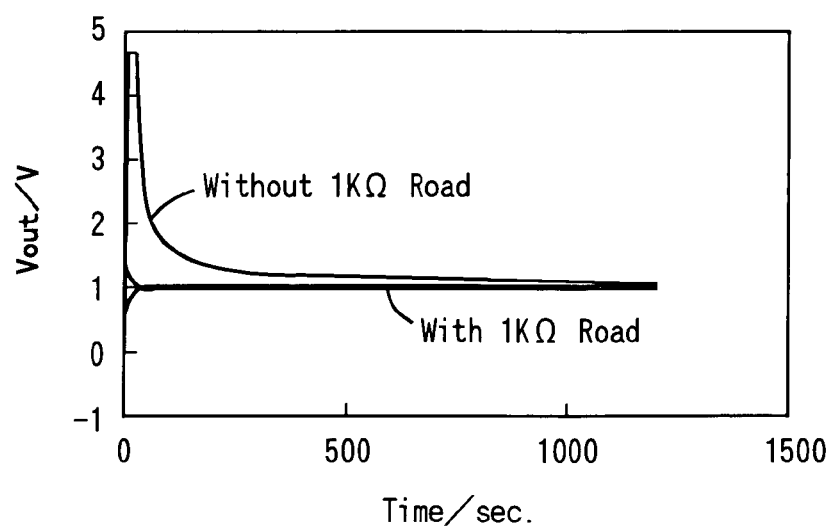
FIG. 7 is a characteristic diagram illustrating differences in the output upon turning on the power supply when the gas sensor is provided with a parallel resistor and when it is not provided with a parallel resistor. Before turning on the power supply, the gas sensor was left to stand in CO of 1000 ppm for one hour and then left to stand in air for one hour.

In the embodiment, as a very small voltage is applied to the gas sensor as a test signal, hysteresis is small. FIG. 6 illustrates changes in the output signals of the gas sensor when the self-diagnosis of the embodiment was repeated ten times at an interval of one hour. After repeating self-diagnosis ten times, there were no significant difference in the output. FIG. 7 illustrates the role of the resistance R9 in preventing polarization of the gas sensor when the battery power source is off. Two gas sensors were connected in parallel with a resistor R9 of 1 kΩ, respectively, and other two gas sensors were not provided with any parallel resistor. They were left to stand in CO of 1000 ppm without power source for one hour. After that, they were left to stand in clean air for one hour, then they were assembled in the gas detection circuit of the embodiment, and the battery power source was turned on. FIG. 7 illustrates the output waveform at the time. In the case of no parallel resistance, it takes about ten minutes from turning on the battery power source until the sensor signal is stabilized. In contrast to it, when a parallel resistance is provided, detection of gas can be started, for example, within one minute.

It may be arranged that the transistor Tr2 is not provided and a test is directly applied from the input/output 28 to the opposite side of the gas sensor 2 of the resistor R10. Square wave is used as the waveform of the test signal, but the waveform is discretionary. The gas sensor 2 may be assembled into the circuit of FIG. 2 by reversing the sensing electrode S and the counter electrode C, and the amplifying circuit or the like of FIG. 2 may be modified accordingly.

In the embodiment, the following merits are obtained.
(1) The state of the electrochemical gas sensor can be sorted out into normal state, short-circuited state, abnormal state of breaking of wire or deteriorated catalyst, etc.
(2) The test signal that is applied in self-diagnosis is as very small as 1 mV×10 seconds, and the time required for self-diagnosis is within one minute. No hysteresis remains, and a test voltage can be easily produced by means of a fixed resistor R9. When the test signal is made smaller or shorter, the time required for self-diagnosis can be shortened more.
(3) It is sufficient to add a test signal applying circuit with the conventional amplifying circuit of an electrochemical gas sensor. Hence there is no need of assembling a gas sensor into a special amplifying circuit for self-diagnosis.

Best Mode

Figure 8:
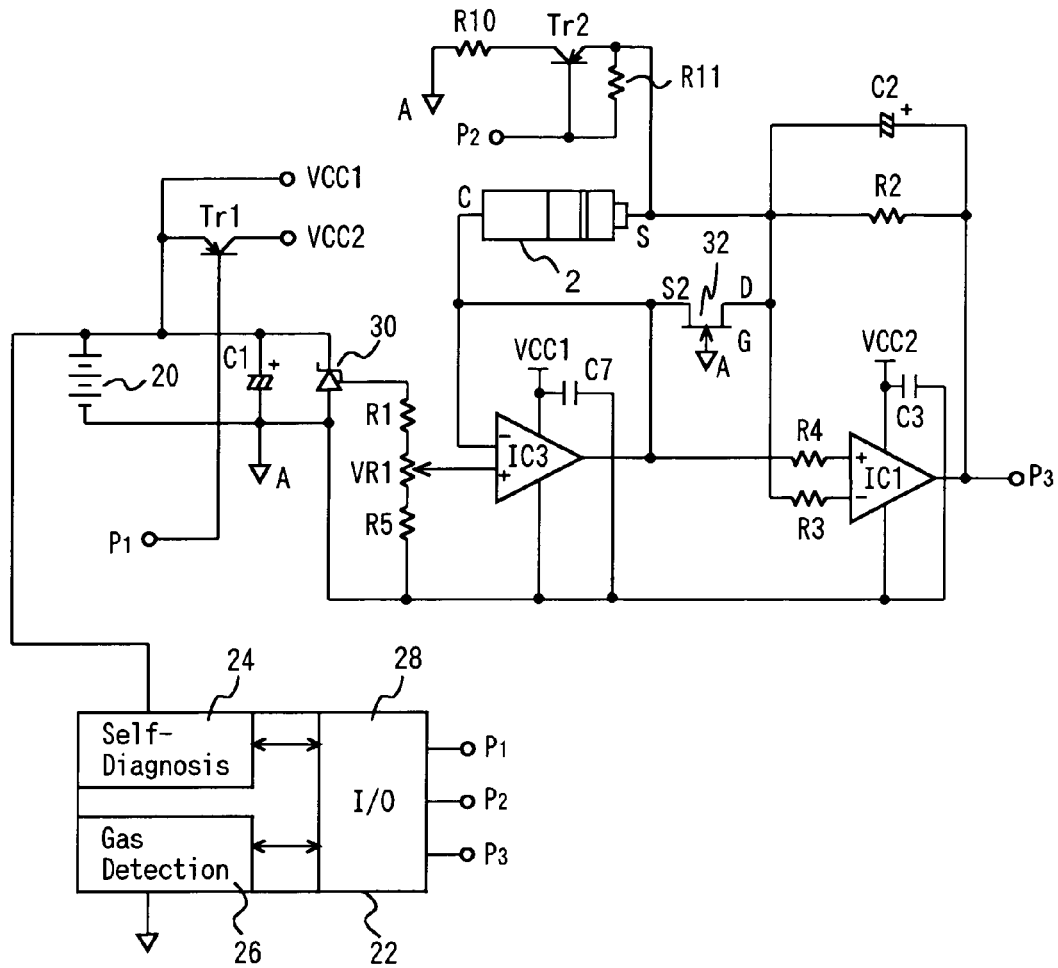
FIG. 8 is a circuit diagram of the best embodiment.
Figure 9:
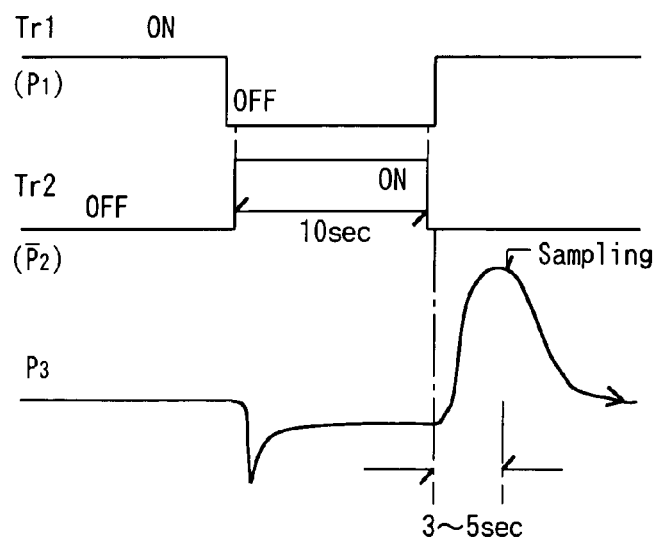
FIG. 9. is a timing chart of the best embodiment.

FIG. 8 and FIG. 9 illustrate the best embodiment. It is similar to the embodiment of FIG. 1 through FIG. 7 except some points set forth, and the same marks denote the same things. An operational amplifier IC3 keeps the counter electrode of the gas sensor 2 at a constant potential of, for example, about 1.5 to 2 V, and it is operated by a power source Vcc1 that is not controlled by the transistor Tr1. C7 denotes a capacitor. 32 denotes an FET switch, and when the potential difference between the source S2 and the gate G is around zero, the resistance between the source S2 and the drain D is about 50 Ω, and when the difference is 1.5 V or over, the resistance is at a M Ω level. The FET switch 32 will open when the power source of the detection circuit is turned on, and the FET switch 32 will close when the power source is turned off. In this way the FET switch 32 prevents polarization of the gas sensor 2 when it is left to stand. The operational amplifier IC2 is connected to the power source Vcc2 that goes through the transistor Tr1, and the operational amplifier IC2 of FIG. 2 was not provided.

The operations of the best embodiment of FIG. 8 are illustrated in FIG. 9. The transistor Tr1 is turned off, for example, for ten seconds, and during this time, the transistor Tr2 is turned on for a time span that is narrower on both the rise and the decay, for example, by 0.1 to 1 second than the off period of the transistor Tr1. When turning off the transistor Tr1, the operating amplifier IC1 turns off, and when turning on the transistor Tr2, a test signal is applied to the gas sensor 2. During this time, the FET switch 32 remains in its off state and is not involved with self-diagnosis. Self-diagnosis is done similarly to that of the circuit of FIG. 2. For example, at 3rd to 5th second after turning on the transistor Tr1 again, the signal P3 is sampled, and if it is in a predetermined voltage range, for example, 2 to 4 V, the sensor 2 is judged to be in good condition.

As to the FET switch 32 for preventing polarization, the gate G is connected to the earth A, and when the power source Vcc1 is turned off, the FET switch 32 will close, and when the power source Vcc1 is turned on, the FET switch 32 will open to cancel the offset of the operational amplifier IC1. In the circuit of FIG. 2, as two inputs of the operational amplifier IC1 are connected by the resistor R9, an offset is generated in the output of the operational amplifier IC1. In FIG. 8, two inputs are connected by the gas sensor 2 of a non-ohmic element, thus the offset can be made smaller. Accordingly, an operational amplifier having a large offset can be used, and the circuit cost is reduced significantly.

Figure 10:
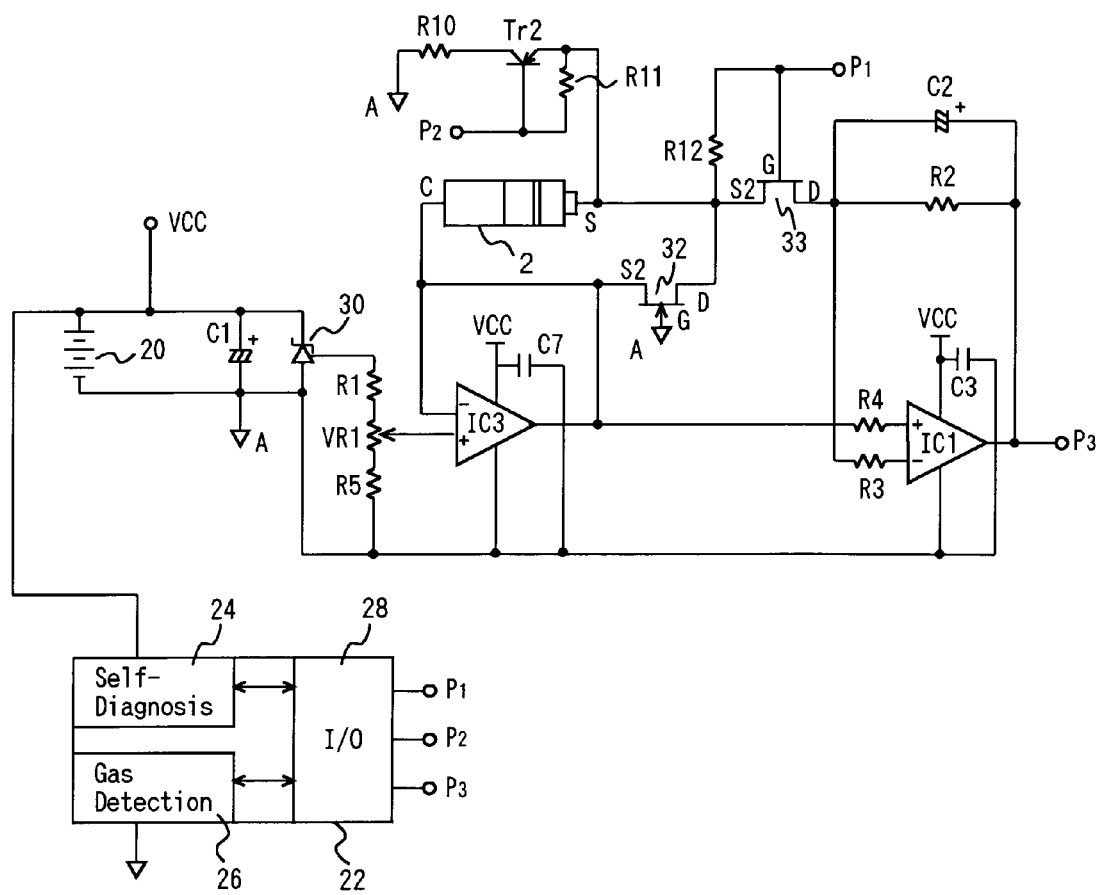
FIG. 10 is a circuit diagram of the third embodiment.

FIG. 10 illustrates a modification of the best embodiment. 33 denotes an FET switch that is similar to the FET switch 32, and S denotes a source, D denotes a drain, and G denotes a gate, respectively. R 12 denotes a large resistor of about 1 Ω. The FET switch 33 is opened by the signal P1 to disconnect the sensor 2 from the operational amplifier IC1. During the duration of the signal P1, the test signal P2 is applied. The modification is similar to the best embodiment in other aspects. In FIG. 10, the two operational amplifiers IC1 and IC2 may be driven with a common power source Vcc. Therefore, a package including two operational amplifiers may be used for the operational amplifiers IC1 and IC2. In contrast with this, in FIG. 8, the operational amplifiers IC1 and IC2 may be driven respectively with two power sources. Therefore, the circuit for these power sources can not be in common, so that two packages for the operational amplifiers are necessary.

The invention claimed is:

1. A gas detecting device having an electrochemical gas sensor having at least a sensing electrode and a counter electrode connected to a solid or liquid electrolyte, and an amplifying circuit for amplifying the output of the gas sensor to detect a gas, wherein said gas sensor is self-diagnosed upon the output of said gas sensor upon applying an electrical test signal thereto,
   the gas detecting device further comprising:
   test signal applying means for applying the test signal to the gas sensor when the amplifying circuit is not operating;
   sampling means for starting up said amplifying circuit when said test signal turns off and for sampling the output of said amplifying circuit within a predetermined period after said startup; and
   self-diagnosing means for self-diagnosing said gas sensor upon the output of the sampling means.

2. A gas detecting device according to claim 1, wherein the self-diagnosing means diagnoses said gas sensor as normal when the output of the sampling means is within a predetermined range different from the output in clean air and diagnoses said gas sensor as abnormal when the output of the sampling means is within a second predetermined range in the vicinity of the output in clean air or in the vicinity of both ends of the output range of said amplifying circuit.

3. A gas detecting device according to claim 2, either one electrode of the sensing electrode or the counter electrode of the gas sensor being kept at a constant potential by means of the power source of the gas detecting device, the other electrode of the gas sensor being connected to the input of an operational amplifier of said amplifying circuit, and said device further comprising an FET switch having a source, a drain, and a gate arranged in parallel with the gas sensor and opening when the voltage between the source and the drain is not less than a predetermined value, wherein the gate is arranged so that the voltage is not less than the predetermined value when the power source is on and is less than the predetermined value when the power source is off.

4. A gas detecting device according to claim 3, further comprising a switch, opening while a test signal is being applied, between said the other electrode and the input of the operational amplifier.

5. A gas detecting device according to claim 3, wherein the test signal applying means applies the test signal from said the other electrode into the gas sensor.

6. A gas detecting device according to claim 1, further comprising a resistor connected in parallel with said gas sensor.

* * * * *